(12) United States Patent
Cannon et al.

(10) Patent No.: US 8,951,275 B2
(45) Date of Patent: Feb. 10, 2015

(54) TROCAR FOR USE DURING ENDOSCOPY

(75) Inventors: Jeremy Cannon, Boston, MA (US); Pedro Del Nido, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 498 days.

(21) Appl. No.: 10/580,144

(22) PCT Filed: Nov. 22, 2004

(86) PCT No.: PCT/US2004/039383
§ 371 (c)(1),
(2), (4) Date: May 18, 2006

(87) PCT Pub. No.: WO2005/051175
PCT Pub. Date: Jun. 9, 2005

(65) Prior Publication Data
US 2007/0149931 A1    Jun. 28, 2007

Related U.S. Application Data

(60) Provisional application No. 60/523,708, filed on Nov. 20, 2003.

(51) Int. Cl.
*A61B 17/34* (2006.01)
*A61B 19/00* (2006.01)
*A61B 17/00* (2006.01)

(52) U.S. Cl.
CPC ......... *A61B 17/3421* (2013.01); *A61B 17/3417* (2013.01); *A61B 17/3462* (2013.01); *A61B 17/3498* (2013.01); *A61B 17/3474* (2013.01); *A61B 17/3476* (2013.01); *A61B 19/38* (2013.01); *A61B 2017/00243* (2013.01); *A61B 2017/3437* (2013.01); *A61B 2017/3441* (2013.01)

USPC .......................................... 606/185

(58) Field of Classification Search
USPC ......... 606/185, 191, 194, 190, 184, 167, 159; 604/164.02, 264, 321, 323, 258, 259, 604/167.01–167.06, 170, 164.01, 164.12, 604/96.01, 164.03–164.09, 158, 160, 604/164.11, 170.02, 171, 506, 507, 173, 604/540, 267, 268, 43, 45, 93.01, 48, 508, 604/902, 903, 35
See application file for complete search history.

(56) References Cited

U.S. PATENT DOCUMENTS

| | | | | |
|---|---|---|---|---|
| 4,180,068 A | * | 12/1979 | Jacobsen et al. | 604/44 |
| 5,256,149 A | * | 10/1993 | Banik et al. | 604/164.01 |
| 5,279,551 A | * | 1/1994 | James | 604/44 |
| 5,352,206 A | * | 10/1994 | Cushieri et al. | 604/170.01 |
| 5,454,791 A | * | 10/1995 | Tovey et al. | 604/118 |
| 5,458,633 A | * | 10/1995 | Bailey | 604/164.01 |
| 5,622,626 A | | 4/1997 | Matkovich | |
| 5,658,298 A | * | 8/1997 | Vincent et al. | 606/139 |
| 5,752,970 A | * | 5/1998 | Yoon | 606/185 |
| 5,788,676 A | * | 8/1998 | Yoon | 604/167.03 |

(Continued)

FOREIGN PATENT DOCUMENTS

WO         98/40016 A2    9/1998

*Primary Examiner* — Jocelin Tanner
(74) *Attorney, Agent, or Firm* — Fish & Richardson P.C.

(57) ABSTRACT

According to the present invention, there is provided a trocar including an insert end, the insert end including a fluid and airtight chamber. Also provided is a method of maintaining a fluid and airtight environment when introducing a surgical instrument into a patient by inserting the instrument into the patient through a fluid and airtight chamber of a trocar.

23 Claims, 4 Drawing Sheets

(56) References Cited

U.S. PATENT DOCUMENTS

| | | | |
|---|---|---|---|
| 5,968,060 A * | 10/1999 | Kellogg | 606/169 |
| 5,993,471 A * | 11/1999 | Riza et al. | 606/185 |
| 6,017,333 A * | 1/2000 | Bailey | 604/264 |
| 6,287,280 B1 | 9/2001 | Lampropoulos | |
| 6,379,326 B1 * | 4/2002 | Cimino | 604/35 |
| 6,520,939 B2 * | 2/2003 | Lafontaine | 604/167.03 |
| 6,685,665 B2 * | 2/2004 | Booth et al. | 604/26 |
| 2002/0111585 A1 | 8/2002 | LaFontaine | |
| 2002/0161378 A1 | 10/2002 | Downing | |
| 2004/0191897 A1 * | 9/2004 | Muschler | 435/325 |

* cited by examiner

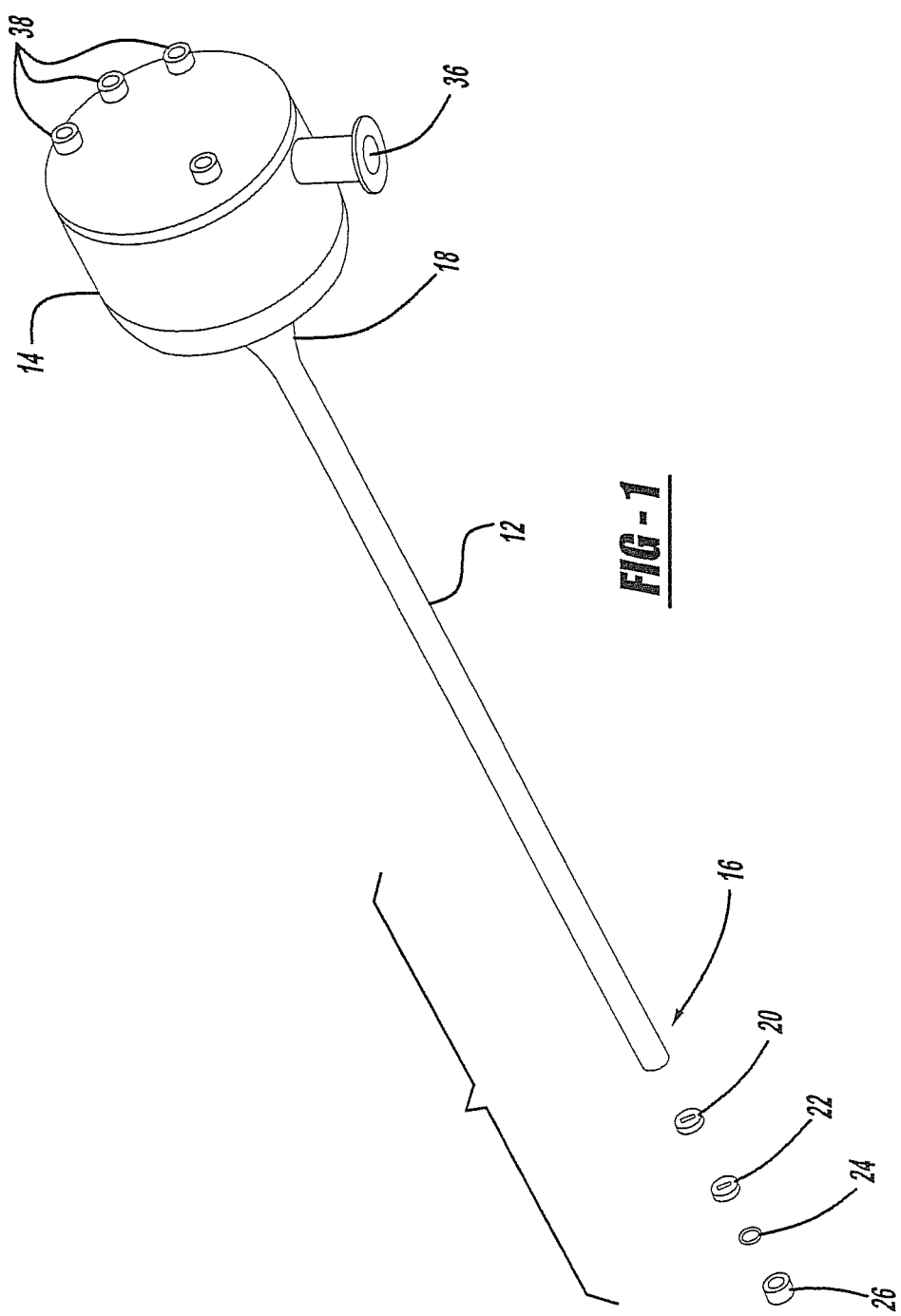

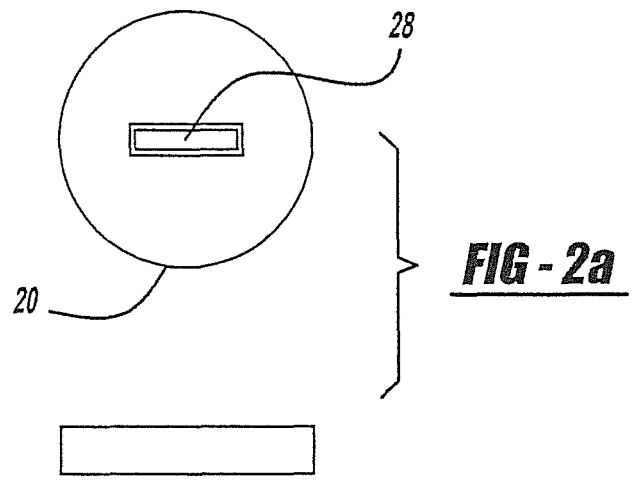
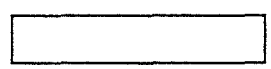
FIG - 2a
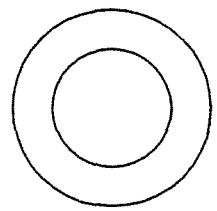
FIG - 2b
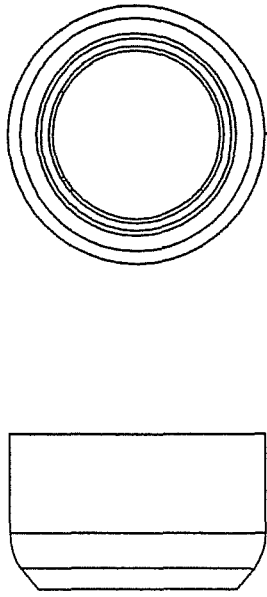
FIG - 2c

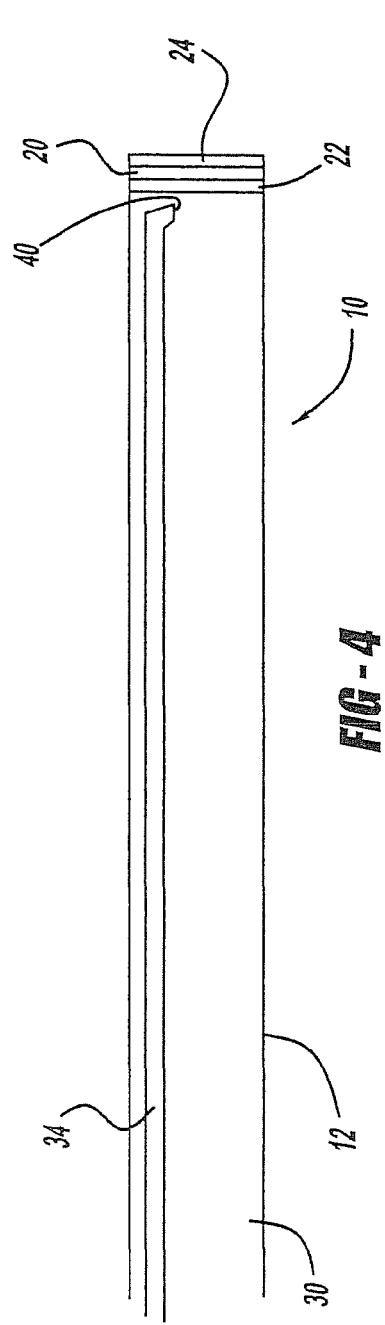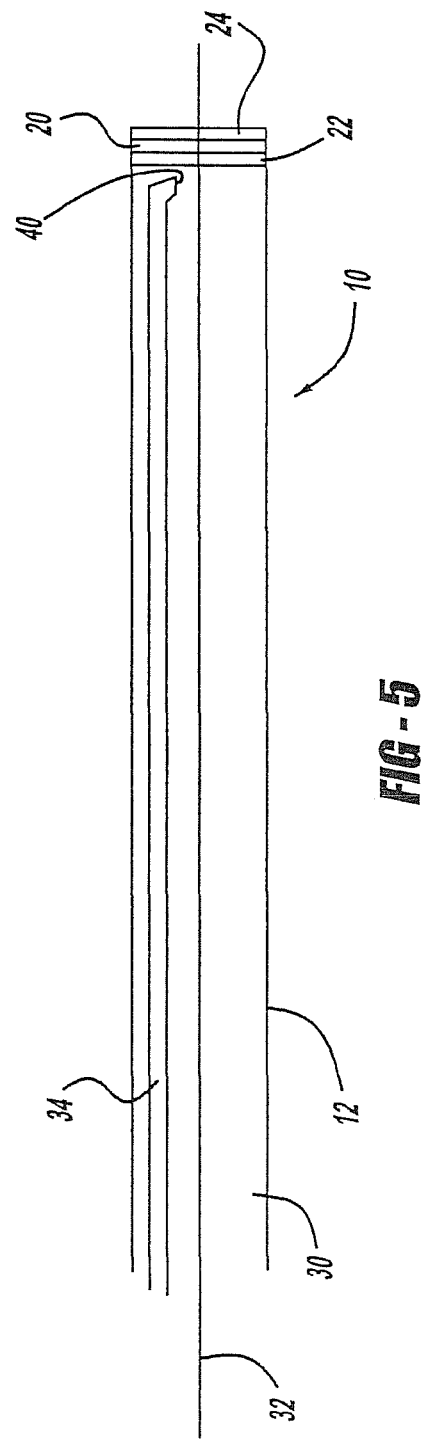

TROCAR FOR USE DURING ENDOSCOPY

CROSS-REFERENCE TO RELATED APPLICATIONS

This is a National Phase Filing Under 35 U.S.C. 371, of International Application No. PCT/US04/39383, filed Nov. 22, 2004, which claims the benefit of priority of U.S. Provisional Patent Application Ser. No. 60/523,708, filed Nov. 20, 2003, both of which are incorporated herein by reference.

BACKGROUND OF THE INVENTION

1. Field of the Invention

Generally, the present invention relates to surgical instruments. More specifically, the present invention relates to trocars that can be used in conjunction with other surgical instruments.

2. Description of Related Art

For many years most surgery was performed using an open field technique. The surgeon made an incision dictated by the need to directly observe the area or field of interest and to insert his or her hand or hands, and/or one or more instruments therein to perform manipulations within the body cavity accessed through the incision. Retractors and assistants help to provide means of access. For many procedures these incisions are as long as 20 centimeters, traumatic, and painful. This translates into a painful recovery, prolonged hospitalization with a slow return to a normal functional state, and significant cost.

An alternative to open surgery, endoscopic surgery, has also been available for many years, though not as widely applied. Through an endoscope, a tubular optical system for viewing the interior of an organ or body cavity, tissues can be observed. An endoscope is used by making a small incision in the appropriate body covering. A hollow tube, or port, usually 10-25 cm in length and 5-30 mm in diameter, is placed through the incision and the endoscope is placed through the hollow tube. Through various other incisions and ports, other instruments can be placed into a body space for manipulation, grasping, cutting, coagulation etc., similar to open surgery. In the abdomen and pelvis, the optical tube is called a laparoscope and the method is referred to as laparoscopic surgery.

Laparoscopic surgery usually includes a step of expanding the body cavity with air, inducing a state of pneumoperitoneum, which enhances the surgeon's view and ability to make manipulations. This is accomplished by one of two techniques, air insufflation or abdominal wall lifting. Abdominal wall lifting creates negative pressure within the cavity in relation to the atmosphere, drawing in air through a small incision when the wall is lifted. The disadvantage with this technique is that observation is imperfect. A tent is created with a central peak and a collapsed perimeter. Though most-structures have midline attachments, most endoscopic manipulations take place in the periphery. This is where visualization with this technique is worst. Insufflation is a positive pressure system using a medicinal vapor such as carbon dioxide or nitrogen injected into the peritoneal cavity to balloon the abdominal wall. Expansion is more uniform; vision is better. This is the most widely used technique. Because of the positive pressure, however, the abdomen must be sealed to maintain expansion. This requires that all incisions and ports be sealed. Insufflation also has adverse respiratory and hemodynamic consequences due to positive pressure inhibiting chest expansion and venous blood return to the heart.

Though endoscopic surgery has been available for many years, its application has recently increased due primarily to the development of video monitoring equipment. This has allowed all members of the surgical team to observe, though indirectly, what only the surgeon could previously observe through a laparoscope. In some cases visualization is better than with direct observation. This has led to renewed interest and investigation of these techniques.

The benefit of endoscopic surgery is the limited incisional trauma, improved cosmesis, and decreased pain. For several simple techniques, such as laparoscopic cholecystectomy, this has translated into decreased hospitalization and earlier return to normal function, though cost savings is debated.

While some open surgical procedures have been adapted to laparoscopic technique, there are limitations with this method, particularly with more complex procedures. Fundamental problems relate to the access tubes used for inserting the various manipulative instruments. While limiting incisional trauma, the small diameter of these tubes dictates and limits the design of the inserted instruments. To achieve similar function as in open surgery, equipment becomes complex and therefore more expensive. There is also added risk with each access tube. Each tube requires a stab-wound of the body wall, risking injury to contained viscera with each puncture.

Equally important has been the impact on the surgeon's ability to manipulate tissue. While the visual field may have been improved, tactile sensation, depth perception, and proprioceptive awareness of tissues have been markedly reduced by instruments that insulate the surgeon from the operative field. As the surgeon continually confirms that that which is done is that which is desired, procedural and anesthesia time increase. Furthermore, the limited access enabled by each port dictates that multiple ports be used. As procedural complexity increases, the surgeon must adapt to a continuously changing and less predictable environment than with simple procedures. The number of ports, and the risk and incidence of complications increases. The requirement for highly skilled and coordinated surgical teams also increases. This has resulted in long learning curves and has limited wide application of these procedures for complex cases.

One device in common usage to establish relatively small incisions for the insertion of equipment therethrough is the trocar. The trocar has a sharp end designed to pierce the skin as the surgeon presses it down to pierce through the skin. It may also pierce the underlying viscera unless great care is taken, particularly in view of the flexibility of the body wall. The trocar includes a cannula or tube used for drainage or for the insertion of a device into the body cavity. Since it is desirable to minimize the patient's wounds, there is an effort made to minimize the size of an incision associated with trocar use. As a result, the size of the tube used in the trocar-created incision is generally relatively small. It therefore can only be used to pass relatively small devices into the body cavity. Moreover, the narrow tube severely restricts maneuverability of the device contained therein. Therefore, though trocars offer the advantage of wound minimization, they are of some danger to the viscera, they are of restricted dimensions for allowing the passage of devices of interest there through, and they permit limited tactile manipulation.

There has been concern about wound contamination during laparoscopic surgery, particularly the implantation of tumor cells. The etiology of this problem is unclear. It may be a systematic problem with a particular element of the technique, such as insufflation where positive pressure venting through the incision results in contamination. Another systematic problem might be direct contamination during specimen removal. The anecdotal occurrence of these problems suggests a more isolated and less systematic error, such as poor tissue handling technique. However, these concerns and the lack of understanding have limited the application of the technique.

It would therefore be useful to develop a surgical instrument that enables endoscopy to be utilized in more delicate surgeries. More specifically, it would be useful to develop an instrument that enables endoscopy to be used without concern for contamination of the tissue wherein the surgery is being performed. For example, major heart surgery has been accomplished by procedures that require full cardiopulmonary bypass (CPB), and complete cessation of cardiopulmonary activity. Open-heart surgery typically requires significant hospitalization and recuperation time for the patient. The average mortality rate with this type of procedure is low, but is associated with a complication rate that is often much higher compared to when cessation and CPB are not required. While very effective in many cases, the use of open-heart surgery to perform various surgical procedures such as coronary artery bypass grafting (CABG) is highly traumatic to the patient. These procedures require immediate postoperative care in an intensive care unit, a period of hospitalization for at least several days, and an extended recovery period. In addition, open-heart procedures require the use of CPB, which continues to represent a major assault on a host of body systems. For example, there is noticeable degradation of mental faculties following such surgeries in a significant percentage of CABG patients. This degradation is commonly attributed to cerebral arterial blockage and emboli from debris in the blood generated by the use of CPB during the surgical procedure. At the same time, the dramatic increase in the life expectancy of the general population has resulted in patients that are more likely to be older and in poor health, with less cardiovascular, systemic, and neurologic reserve needed to recover from the trauma caused by the use of CPB. As a consequence, inflammatory, hemostatic, endocrinologic, and neurologic stresses are tolerated to a much lesser degree by a significant number of patients today, and play a more significant role in CPB-induced morbidity.

The CABG procedure generally involves open chest surgical techniques to treat diseased vessels. During this procedure, the sternum of the patient is cut in order to spread the chest apart and provide access to the heart. During surgery the heart is stopped, and by the use of CPB, blood is diverted from the lungs to an artificial oxygenator. During CABG procedures, a source of arterial blood is connected to a coronary artery downstream from the occlusion. The source of blood is often an internal mammary artery, and the target coronary artery is typically among the anterior or posterior arteries, which may be narrowed or occluded. The same or similar CPB procedure is used in conjunction with other cardiac surgical procedures, such as value repair or replacement and heart transplant.

The combined statistics of postoperative morbidity and mortality continue to illustrate the shortcomings of CPB. The extracorporeal shunting and artificially induced oxygenation of blood activates a system wide roster of plasma proteins and blood components in the body including those that were designed to act locally in response to infection or injury. When these potent actors are disseminated throughout the body without normal regulatory controls, the entire body becomes a virtual battleground. The adverse hemostatic consequences of CPB also include prolonged and potentially excessive bleeding. CPB-induced platelet activation, adhesion, and aggregation also contribute to depletion in platelet number, and are further compounded by the reversibly depressed functioning of platelets remaining in circulation. The coagulation and fibrinolytic systems both contribute to hemostatic disturbances during and following CPB. However, the leading cause of morbidity and disability following cardiac surgery is cerebral complications. Gaseous and solid micro and macro emboli, and less often perioperative cerebral hypoperfusion, produce neurologic effects ranging from subtle neuropsychologic deficits to fatal stroke. Advances in computer tomography, magnetic resonance imaging, ultrasound, and other imaging and diagnostic techniques have added to the understanding of these complications. But with the possible exception of perioperative electroencephalography, these technologies do not yet permit real time surgical adjustments that are capable of preventing emboli or strokes in the making. Doppler and ultrasound evaluation of the carotid artery and ascending aorta, and other diagnostic measures, can help identify surgical patients at elevated risk for stroke and are among the growing list of pharmacologic and procedural measures for reducing that risk.

CPB also affects various endocrine systems, including the thyroid gland, adrenal medulla and cortex, pituitary gland, pancreas, and parathyroid gland. These systems are markedly affected not only by inflammatory processes, but also by physical and biochemical stresses imposed by extracorporeal perfusion. Most notably, CPB is now clearly understood to induce euthyroid-sick syndrome that is marked by profoundly depressed triiodothyronine levels persisting for days following cardiothoracic surgery. The efficacy of hormone replacement regimens to counteract this effect, are currently undergoing clinical investigation. By contrast, levels of the stress hormones epinephrine, norepinephrine, and cortisol are markedly elevated during and following CPB, and hyperglycemia is also possible.

Alternatives to CPB are limited to a few commercially available devices that may further require major surgery for their placement and operation such as a sternotomy or multiple anastomoses to vessels or heart chambers. For example, some present day devices used in CPB may require a sternotomy and an anastomosis to the ascending aorta for placement. The main drawbacks of these devices include their limited circulatory capacity, which may not totally support patient requirements, and their limited application for only certain regions of the heart, such as a left ventricular assist device. Other available devices that permit percutaneous access to the heart similarly have disadvantages, such as their limited circulatory capabilities due to the strict size constraints for their positioning even within major blood vessels. Moreover, the relative miniaturization of these types of devices present a high likelihood of mechanical failure. In further attempts to reduce the physical dimensions for cardiac circulatory apparatus, the flow capacity of these devices is significantly diminished.

During cardiac surgery, the heart is either beating, in which case the heart continues to circulate the blood through the lungs to maintain the patient, or immobilized entirely in which case oxygenation and circulation of blood to maintain the patient requires use of CPB. Bypass surgery on a beating heart has been limited to only a small percentage of patients requiring the surgical bypass of an occluded anterior heart vessel. These patients typically could not be placed on CPB and were operated on while the heart was kept beating. These patients are at risk of having to be placed on CPB on an emergency basis in the event the heart stops or becomes unstable or is damaged during the surgical procedure on the beating heart. Meanwhile, patients requiring surgery on posterior or lateral heart vessels and whose hearts must be immobilized and placed on CPB often suffer major side effects as previously described.

The medical community is currently performing more beating heart bypass surgery in an effort to avoid the use of artificial heart-lung machines. The need is increasing for apparatus systems, methods and associated equipment to enhance the capability and versatility of beating heart surgery and to avoid CPB procedures in any heart surgery. The current trend toward thoracoscopic methods of performing bypass surgery, without opening the chest cavity, have resulted in limited success and applicability primarily due to the limited number of heart vessels which can be accessed through thoracoscopic methods. A major limitation of thoracoscopic bypass surgery methods is due to the fact that only the anterior heart vessels are accessible for surgery. More importantly, even open chest surgery providing full access to the heart also requires CPB when bypass surgery is performed on the lateral or posterior vessels of the heart, due to the fact that in conventional procedures the heart must be stopped when it is lifted or rotated from its normal position and manipulated for surgical access to the various heart vessels. Obviously, the heart is also stopped when valve repair or replacement is performed and when heart transplant is performed.

Further, tens of thousands of people are born each year with congenital defects of the heart. Some of the more common types of congenital cardiac defects include atrial septal defect (ASD), ventricular septal defect (VSD), and patent ductus arteriosis (PDA). An ASD is a hole in the cardiac septum between the left and right atria, while a VSD is a hole in the septum between the left and right ventricles. Patent ductus arteriosis is incomplete closure of the opening between the pulmonary artery and the aorta that is present during fetal development. These conditions may cause blood to abnormally shunt from the right side of the heart to the left side of the heart without being properly oxygenated in the lungs, so that the body tissues supplied by the blood are deprived of oxygen. In addition, blood in the left side of the heart may shunt back to the right side through the defect rather than being pumped into the arterial system, causing abnormal enlargement of the right chambers of the heart.

ASD's, VSD's and PDA can frequently be surgically repaired with significant success. Smaller defects may be repairable by simply suturing the defect closed, while larger defects may require a patch of polyester, expanded polytetrafluoroethylene, or a portion of the patient's own pericardium to be sutured into the heart to cover and occlude the defect.

Ordinarily, such surgery is performed using open-chest techniques while the heart is under cardioplegic arrest and circulation is maintained by cardiopulmonary bypass. Using such techniques, a gross sternotomy or thoracotomy is created in order to gain access to the heart and great vessels, facilitating clamping and cannulation of the aorta for inducing cardioplegic arrest, and allowing instruments to be introduced into the chest cavity and into the heart to perform the surgical repair. The necessity of stopping the heart significantly heightens the risks attendant such procedures, particularly the risks of causing ischemic damage to the heart muscle, and of causing stroke or other injury due to circulatory emboli produced by aortic clamping and vascular cannulation. In addition, the creation of a gross thoracotomy produces significant morbidity and mortality, lengthens hospital stay and subsequent recovery, increases costs, and worsens the pain and trauma suffered by the patient. Moreover, many congenital defects are repaired in children under the age of ten years for whom the morbidity and mortality of open-chest surgery and cardioplegic arrest can be even greater than for older patients.

In an effort to avoid the necessity of grossly opening the chest and stopping the heart, a number of intravascular devices have been developed for repair of ASD's, VSD's, and PDA. For example, U.S. Pat. No. 3,874,388 to King et al. discloses an intravascular delivery catheter introduced intraluminally from a peripheral vein into the right side of the heart which can be used to position an artificial umbrella-like patch across a septal defect and to anchor the patch to the cardiac septum. Other intravascular delivery devices and artificial patches for the repair of septal defects can be seen in U.S. Pat. No. 5,334,217, U.S. Pat. No. 5,284,488, U.S. Pat. No. 4,917,089, U.S. Pat. No. 4,007,743, and PCT Application No. PCT/US92/10141.

While intravascular approaches to the repair of congenital defects can provide certain advantages, the most significant of which is the elimination of the need for gross thoracotomy and cardioplegic arrest, these techniques have suffered from a number of problems. One such problem is the difficulty in manipulating the artificial patches into position across a defect using only the proximal end of a long and flexible delivery catheter positioned through a tortuous right lumen. Also problematic is the inadequacy of fixation of endovascularly-placed patches, creating a tendency of such patches to migrate or embolize after placement, which can allow blood to again shunt through the defect. In addition, once such a patch has been placed and the delivery catheter detached from the patch, relocating and repositioning the patch with the catheter is difficult, if not impossible, and may require open surgical correction. Moreover, in young children, the size of the peripheral vessels is extremely small, and damage to such vessels could have serious effects upon the growth of the child. Thus, the size of the devices that can be introduced through such vessels is greatly limited.

In addition to ASD, VSD, and PDA, various other types of cardiac disease also may be diagnosed and treated by intervention within the interior chambers of the heart. For example, some cardiac arrhythmias such as ventricular tachycardias, supraventricular tachycardias, and atrial fibrillation, may be diagnosed by obtaining access into an interior chamber of the heart and by performing electrophysiological mapping to identify abnormal conduction pathways. Once these abnormal conduction pathways are identified, in some cases the disease may be treated by ablating selected cardiac tissue using radiofrequency (RF) energy or a medical laser to eliminate the abnormal pathways. A number of endovascular approaches have been developed which attempt to allow intracardiac mapping and ablation using catheters introduced transluminally from peripheral vessels into the heart. Such devices are disclosed, for example, in U.S. Pat. Nos. 4,960,134, 4,573,473, 4,628,937, and 5,327,889. However, endovascular mapping and ablation devices suffer from many of the same problems suffered by endovascular septal defect repair devices, including a lack of control and precise positionability from the proximal end of these highly flexible and elongated devices, the significant size constraints of peripheral vessels, and the inability to position the devices in all potentially diseased sites within the heart.

What are needed, therefore, are devices and methods to enable the repair of ASD, VSD, PDA, and other congenital defects, as well as cardiac arrhythmias and other diseases of the heart, which eliminate the need for gross thoracotomy and cardioplegic arrest, but which overcome the aforementioned problems with intravascular techniques. The devices and methods should facilitate a high level of control for precise manipulation within the heart. The devices and methods should produce a septal defect or PDA repair that is reliable and long-lasting, and should not be susceptible to migration, embolization, or reopening of a defect. The devices and methods for septal defect and PDA repair should allow the position of a repair patch to be inspected after initial placement and to be repositioned if necessary. Finally, the devices and methods should not risk damaging the peripheral vessels of the patient, nor should the size and configuration of the devices be limited by the size of the patient's peripheral vessels.

SUMMARY OF THE INVENTION

According to the present invention, there is provided a trocar including an insert end, the insert end including a fluid and airtight chamber. Also provided is a method of maintaining a fluid and airtight environment when introducing a surgical instrument into a patient by inserting the instrument into the patient through a fluid and airtight chamber of a trocar.

BRIEF DESCRIPTION OF THE DRAWINGS

Other advantages of the present invention are readily appreciated as the same becomes better understood by reference to the following detailed description when considered in connection with the accompanying drawings wherein:

FIG. 1 is a perspective view of the trocar of the present invention;

FIG. 2 is a cut-away view of the seals and gasket/o-ring of the present invention;

FIG. 4 is a side view broken away of the lumen of the trocar of the present invention in the neutral position; and FIG. 5 is a side view broken away of the lumen of the trocar of the present invention in the engaged position.

DETAILED DESCRIPTION OF THE INVENTION

Figure 3:
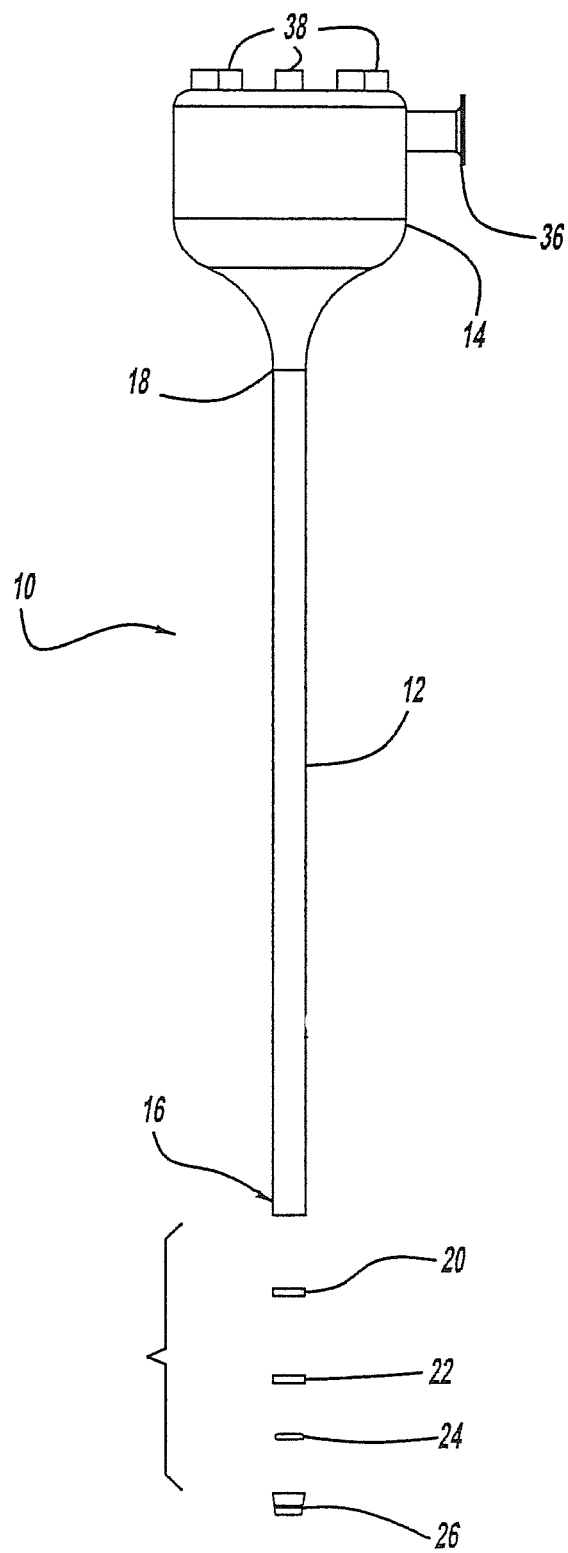
FIG. 3 is a side view of the trocar of the present invention.

Generally, the present invention provides a trocar 10, generally shown at 10 in the figures, that includes an insertion end 16 that is both fluid and airtight. That is, the insertion end 16 includes structure, described below, that perfects a seal at the insertion end 16 of the trocar 10 whether or not an instrument 32, such as a surgical device, extends through the trocar 10.

The trocar 10 of the present invention is preferably formed in a manner known to those of skill in the art. The trocar 10 can be formed of a rigid or a resilient plastic, from a metal, such as 304 or 316 stainless steel, or of any desired material suitable for use as a trocar 10. For example, the trocar 10 can be formed of a plastic-metal composite. Alternatively, the trocar 10 can be formed of a plastic material that can be seen through upon the application of ultrasonic technology. The trocar 10 is preferably constructed of material approved by the United States Food and Drug Administration for use in surgical procedures, that the materials be durable, and capable of being sterilized completely for subsequent re-use. It is also anticipated, however, that the trocar 10 can be constructed as a disposable one-time or throw-away device without the need for subsequent resterilization of the trocar 10.

The trocar 10 of the present invention does not necessarily include an ubturator. Instead the trocar 10 can be inserted into a hole created by a knife. Such insertion enables the trocar 10 to be placed in a small hole that can be stretched to accommodate the trocar 10. The benefit of such insertion is that the small hole into which the trocar 10 is inserted also maintains the trocar 10 in position without allowing the trocar 10 to move once inserted.

More specifically, the trocar 10 of the present invention includes a neck 12 and a body 14. The neck 12 and the body 14 are in fluid and airtight communication, such that there is no leakage between the body and the neck 12. Preferably, the body 14 and neck 12 are formed as a single unit. Alternatively, the body 14 and neck 12 can be separate pieces that are capable of being joined to one another. The neck 12 includes two ends; an insertion end 16 that is inserted into the body of the patient and an opposite end 18 that is the location at which the body 14 attaches to the neck 12.

The insertion end 16 includes devices necessary for maintaining a sealed environment within the trocar 10. In other words, within the insertion end 16, there are devices that prevent fluid and foreign bodies present in the neck 12 or body 14 of the trocar 10 from entering the patient into which the trocar 10 is being place while also preventing substances from within the patient from entering the insertion end 16 and neck 12 of the trocar 10.

The trocar 10 of the present invention can also include an agitator. The agitator can be used to facilitate the movement of air bubbles or foreign objects from the insertion end 16 to the opposite end 18. The agitator can be any device that is capable of manipulating the trocar 10 of the present invention in such a way as to move the air or foreign objects away from the body into which the trocar 10 is inserted. For example, the agitator can be a manual device that lightly taps the trocar 10 or the agitator can be an ultrasonic device that causes vibration of the particles within the trocar 10.

In order to form a fluid and air-tight environment within the trocar 10 the insertion end 16 includes a sealing device. In the preferred embodiment, the sealing device is a series of at least two deformable diaphragms or seals 20, 22 and at least one gasket 24. More than two seals 20, 22 and more than a single gasket 24 can be included without departing from the spirit of the present invention. It is this configuration of the seals and gasket that prevents fluid and foreign bodies from entering the body 14 and from blood and other particles from the body 14 from entering the trocar 10. The sealing device can be sized to fit any trocar 10 and ensures a complete seal of the trocar 10 so that insufflation of a body cavity can be maintained when insufflation is used.

In general, the seals 20, 22 are either adjustable so that the seals 20, 22 fit any number of differently sized trocars or are in a plurality of fixed sizes to be selected as required for a particular trocar 10 being used. The seals 20, 22 of the present invention are fabricated of a material and of a thickness sufficient to manipulate the seals 20, 22 into place in the trocar 10. It is expected that a viscoelastic material such as latex is suitable, though metal variations are possible. The seals 20, 22 function to maintain an instrument 32 passed through the trocar 10 in proper sealing engagement within the trocar 10. The seals 20, 22 each include a slit 28. The slit 28 is of a size sufficient to encompass an instrument 32 there through.

In a particular embodiment of the invention, the seals 20, 22 are fixed, non-inflatable devices that are sufficiently compliant so that they can be moved about without causing a loss of sealing contact with the trocar 10. As the device does not have to be pressurized, the possibility of undesirable failure and, therefore, loss of a seal, does not exist. In addition, the seals 20, 22 can also be pliable or compliant, rather than stiff or rigid, so as to provide sufficient sealing of the trocar 10. The portions of the seals 20, 22 running along the interior body wall are no thicker than the outer section and are preferably much thinner, on the order of 0.1 millimeter to 10 millimeters.

The gasket 24 disclosed above is preferably an O-ring. The gasket 24 perfects the fluid and air-tight seal about an instrument 32 within the trocar 10. Any sized gasket 24 that is sized to fit within the trocar 10 can be disposed in the trocar 10 of the present invention. Preferably, the gasket 24 is made of rubber, however other resilient materials can also be used, such materials are known to those of skill in the art. The gasket 24 is sufficiently pliable as to allow instruments 32 to pass there through of a range of cross-sectional diameters while maintaining a perfected seal thereabout.

A trocar tip 26 is disposed at an end of the insertion end 16 furthest from the body 14. The trocar tip 26 is preferably sharp and made of a resilient material such as stainless steel. However, other materials as are known to those of skill in the art can be used as long as the material can be inserted into the human body 14.

Within the trocar 10 there are at least two lumen. These lumen are completely separate from one another. The first is an instrument lumen 30. The instrument lumen 30 is of a size to enable instruments to be placed there through. The instrument lumen 30 extends from an opening in the body 14 through to the insertion end 16 as shown in FIGS. 4 and 5. The instrument lumen 30 ends at the sealing device disclosed above such that the series of seals and gasket 20, 22, and 24 create a fluid tight lumen.

The second lumen a down flow lumen 34, extends from the body 14 and through the wall of the trocar 10. An outlet 40 opens proximate to the instrument lumen 30. The down flow lumen 34 is made of any resilient material that is fluid tight, and is capable of having a fluid flow there through.

The body 14 of the trocar 10 preferably includes an inlet port 36 fluidly connected to the down flow lumen 24. The inlet port 36 enables the flow of an inert fluid through the port 36 into the down flow lumen 40 within the trocar 10. Additionally, the body 14 includes at least one outlet port 38. The outlet port 38 allows air trapped within the body 14 and neck 12 of the trocar 10 to escape from the trocar 10.

In use, an inert fluid, such as saline, is flowed into the down flow lumen 34, via the inlet port 36, out the outlet port 40 proximate to the instrument lumen 30 of the trocar 10. The fluid contacts any substances, such as air bubbles, that are present within the instrument lumen 30 of the trocar. The air bubbles then flow with the fluid up the instrument lumen 30 to the outlet port 38. In other words, fluid is constantly forcibly passed through the instrument lumen 30 of the trocar such that any air bubbles found within the trocar 10 are captured within the fluid and the flow of the fluid carries the air bubbles away from the insertion end 16 of the trocar 10.

Of vital importance in surgery is that air not be allowed to enter the bloodstream of a patient. This is most critical when beating heart cardiac surgery is being performed because the insertion of oxygen into a blood stream can cause a fatal problem for the patient. Thus, the flowing of the fluid into the instrument lumen 30 of the trocar 10 enables air, and any other substances present in the trocar 10, to be removed from the patient, thereby preventing air or other foreign substances from entering the blood stream of a patient.

The sealing device of the trocar 10 ensures that the fluid flowing through the trocar 10 and air bubbles present in the trocar 10 do not enter the patient. In order to accomplish this, the sealing device functions as follows. When in a neutral or non-use condition, the trocar 10 is inserted into the patient during a scoping procedure. As shown in FIG. 4, the seals 20, 22 are in a closed position and the gasket 24 is in a sealing engagement with both of the seals 20, 22. It is vital that the gasket 24 keep the seals 20, 22 in proper engagement, thus preventing any leakage therethrough. Additionally, it is vital that the seals 20, 22 themselves are in a closed position versus an open position. By maintaining the closed position no fluid or air can flow either into or out of the trocar 10. The slits 28 are designed such that no two slits 28 consecutively have the same orientation. The slits 28 center an instrument 32 passing there through because of this configuration. That is, the non-alignment of the slits 28 cooperate as the instrument 32 passes there through to center the instrument 32 as it approaches the gasket 24. Further, in conjunction with the gasket 24 of the present invention, there is created a fluid tight seal whether or not an instrument 32 passes there through. The gasket 24 holds the seals 20, 22 in place and perfects the seal of the trocar 10. Thus, absent the use of a gasket 24, a fluid tight seal could not be created. The seals 20, 22 assist the gasket 24 in limiting the amount of fluid that is able to reach the gasket 24, thus not overwhelming the gasket 24 with enormous pressure. While a rectangular opening is the preferred shape of the slit 28 and as such is shown in the figures, any slit 28 can be used so long as the slit 28 enables the configuration disclosed above while maintaining the integrity of the sealing device.

FIG. 5 shows the neck 12 when an instrument is inserted there through, in an engaged configuration. The instrument 32 is inserted through the instrument lumen 30 within the neck 12 of the trocar 10. The engaged configuration of the seals 20, 22, when an instrument 32 is placed through instrument lumen 30 of the trocar 10, is such that seals 20, 22 are both in an open condition and the gasket 24 is in sealing engagement about the instrument 32. In the open condition the seals 20, 22 allow for the instrument 32 to travel there through while having minimal extraneous openings. In other words, the seals 20, 22 allow the instrument 32 to pass through openings 28 in the seals 20, 22, but limit the translational movement of the instrument 32. This limits the amount of air and fluid that can flow past the seals 20, 22 about the instrument 32. In the engaged position, a first seal 20 opens, then a second seal 22 opens, and then an o-ring or gasket 24 perfects the seal about the instrument 32 as the it passes through the consecutive seal members. Accordingly, when the instrument 32 is being withdrawn, the second seal 22 closes, and then a first seal 20 closes, thus ensuring that there is always a proper air and fluid tight engagement of the trocar 10 within the patient.

Throughout this application, author and year and patents by number reference various publications, including United States patents. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology that has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A trocar comprising:
a body including a proximal end and a distal fluid tight and airtight insert end, the body including:
an instrument lumen within the body and having proximal and distal ends and comprising an outlet port at its proximal end;
a downflow lumen within the body and having proximal and distal ends, wherein the downflow lumen comprises a proximal inlet port and a distal outlet and is arranged adjacent to or within the instrument lumen; and
two or more deformable diaphragms arranged in the insert end to provide the fluid tight and airtight seal;

wherein the instrument lumen and the downflow lumen are configured such that fluid can flow into the proximal inlet port, through the downflow lumen, and out through the distal outlet into the distal end of the instrument lumen, through the instrument lumen, and out of the outlet port at the proximal end of the instrument lumen to carry substances and air bubbles in the instrument lumen out of the trocar body and to prevent substances and air bubbles in the instrument lumen from entering a patient's body.

2. The trocar according to claim 1, wherein the two or more deformable diaphragms comprise slits for the insertion of an instrument through said slits.

3. The trocar according to claim 2, further comprising at least one O-ring arranged to seal around an instrument inserted into the instrument lumen of the trocar.

4. The trocar according to claim 2, wherein the slits on consecutive deformable diaphragms are perpendicular to one another.

5. The trocar according to claim 1, wherein the trocar includes a neck portion for allowing insertion of an instrument therethrough, and
wherein the instrument lumen is configured to carry fluid flow for removing a substance from within the neck portion about an instrument disposed within the neck portion.

6. The trocar according to claim 1, further including an agitator for agitating particles within the trocar, wherein the agitator is operatively connected to the trocar.

7. The trocar according to claim 6, wherein the agitator comprises at least one of a manual agitator and an automatic agitator.

8. The trocar according to claim 7, wherein the automatic agitator comprises an ultrasonic agitator.

9. The trocar according to claim 1, wherein the trocar is formed of a resilient material.

10. The trocar according to claim 9, wherein the resilient material comprises at least one of plastic, metal, and a plastic-metal composite.

11. The trocar according to claim 10, wherein the plastic is a plastic that can be seen through upon application of ultrasound.

12. A method of maintaining a fluid and airtight environment when introducing a surgical instrument into a patient during an endoscopic procedure, the method comprising:
inserting the instrument into the patient through a fluid tight and airtight seal at a distal end of a trocar body, the seal including two or more deformable diaphragms comprising slits, wherein the slits on consecutive deformable diaphragms are perpendicular to one another; and
constantly flowing a fluid into a proximal inlet port of a downflow lumen within the trocar body, through the downflow lumen, and out through a distal outlet at a distal end of the downflow lumen into a distal end of an instrument lumen which is coaxial with the downflow lumen, and through the instrument lumen, and out of an outlet port at a proximal end of the instrument lumen during the endoscopic procedure, thereby carrying substances and air bubbles in the instrument lumen out of the trocar body, and preventing substances and air bubbles in the instrument lumen from entering the patient during the endoscopic procedure.

13. The method according to claim 12, wherein inserting the instrument comprises inserting the instrument through the slits in the two or more deformable diaphragms and through at least one O-ring at the distal end of the trocar.

14. The method according to claim 12, further including creating a hole in the patient for insertion of the trocar.

15. The method according to claim 14, wherein creating a hole includes creating a hole in a cavity of the patient using an obturator.

16. The method according to claim 14, wherein creating a hole includes creating a hole in a cavity of the patient using a knife or scalpel.

17. The method according to claim 14, further including maintaining the trocar in place within the patient.

18. The method according to claim 17, wherein maintaining the trocar in place includes maintaining the trocar in place via the hole created in the patient.

19. The method of claim 12, wherein the endoscopic procedure is beating heart cardiac surgery.

20. A method of removing a substance and air bubbles from an instrument lumen of a trocar during an endoscopic procedure, the method comprising:
sealing a distal insert end of a trocar body with a fluid tight and airtight seal;
constantly flowing fluid into a proximal inlet port of a downflow lumen within the trocar body, through the downflow lumen, and out through a distal outlet port at a distal end of the downflow lumen during the endoscopic procedure; and
carrying the substance and air bubbles from the instrument lumen out of the trocar body with the fluid, thereby preventing the substance and air bubbles from entering a patient's body during the endoscopic procedure.

21. The method according to claim 20, further including inserting an instrument through the instrument lumen and removing the substance and air bubbles from the instrument lumen about the instrument.

22. The method according to claim 20, further including agitating the trocar.

23. The method of claim 20, wherein the endoscopic procedure is beating heart cardiac surgery.

* * * * *